(12) United States Patent
Mo et al.

(10) Patent No.: US 12,390,094 B2
(45) Date of Patent: Aug. 19, 2025

(54) MULTI-DIRECTIONALLY GUIDED ENDOSCOPE

(71) Applicant: HUNAN VATHIN MEDICAL INSTRUMENT CO., LTD., Xiangtan (CN)

(72) Inventors: Wenjun Mo, Xiangtan (CN); Peng Tang, Xiangtan (CN); Guanhua Zhou, Xiangtan (CN)

(73) Assignee: HUNAN VATHIN MEDICAL INSTRUMENT CO., LTD., Xiangtan (CN)

( * ) Notice: Subject to any disclaimer, the term of this patent is extended or adjusted under 35 U.S.C. 154(b) by 707 days.

(21) Appl. No.: 17/765,446

(22) PCT Filed: Dec. 30, 2020

(86) PCT No.: PCT/CN2020/141494
§ 371 (c)(1),
(2) Date: Mar. 31, 2022

(87) PCT Pub. No.: WO2021/136403
PCT Pub. Date: Jul. 8, 2021

(65) Prior Publication Data
US 2022/0361732 A1    Nov. 17, 2022

(30) Foreign Application Priority Data

Dec. 31, 2019  (CN) .......................... 201911405252.1

(51) Int. Cl.
*A61B 1/005*    (2006.01)
*A61M 25/01*    (2006.01)

(52) U.S. Cl.
CPC ....... *A61B 1/0052* (2013.01); *A61M 25/0147* (2013.01)

(58) Field of Classification Search
CPC .............. A61B 1/0052; A61B 1/00073; A61B 1/00135; A61B 1/0057; A61M 25/0147
See application file for complete search history.

(56) References Cited

U.S. PATENT DOCUMENTS

2004/0236316 A1 * 11/2004 Danitz ................... A61B 34/70
                                                        606/1
2005/0075538 A1 *  4/2005 Banik .................. A61B 1/0052
                                                        600/152
(Continued)

FOREIGN PATENT DOCUMENTS

CN        101495045 A     7/2009
CN        102711629 A    10/2012
(Continued)

*Primary Examiner* — Anh Tuan T Nguyen
*Assistant Examiner* — Shankar Raj Ghimire
(74) *Attorney, Agent, or Firm* — Bayramoglu Law Offices LLC

(57) ABSTRACT

A multi-directionally guided endoscope includes an endoscope body. The endoscope body is connected to a catheter. At least four pulling wires are evenly distributed in the endoscope body. One ends of the pulling wires are connected to an end of the catheter away from the endoscope body. The pulling wires are respectively fixed to pulling mechanisms. The pulling mechanisms are respectively sleeved on guide rods. The guide rods are fixed in the endoscope body. The endoscope body is provided with a plurality of elongated grooves. One ends of the pulling mechanisms respectively extend from the elongated grooves. The multi-directionally guided endoscope is provided with pulling mechanisms that are simple in structure, convenient to operate, and accurate and stable to pull.

12 Claims, 5 Drawing Sheets

(56) References Cited

U.S. PATENT DOCUMENTS

| | | | |
|---|---|---|---|
| 2006/0074383 A1* | 4/2006 | Boulais | A61B 1/0057 604/95.04 |
| 2010/0160730 A1* | 6/2010 | Konomura | G02B 23/2476 600/114 |
| 2014/0058363 A1* | 2/2014 | Berkelaar | A61B 34/70 606/1 |
| 2015/0359416 A1* | 12/2015 | Simchony | A61B 1/0055 600/110 |
| 2018/0055589 A1* | 3/2018 | Joseph | A61M 25/0147 |
| 2019/0029502 A1* | 1/2019 | Smith | A61B 1/0057 |
| 2020/0038128 A1* | 2/2020 | Joseph | A61B 34/71 |
| 2022/0095888 A1* | 3/2022 | Sharma | A61B 17/29 |

FOREIGN PATENT DOCUMENTS

| | | |
|---|---|---|
| CN | 202875299 U | 4/2013 |
| CN | 104053393 A | 9/2014 |
| CN | 107529947 A | 1/2018 |
| CN | 110897591 A | 3/2020 |
| EP | 2883491 B1 | 4/2017 |
| JP | S5010717 Y1 | 4/1975 |
| JP | S57157301 U | 10/1982 |
| WO | 2009035051 A1 | 3/2009 |
| WO | 2014192447 A1 | 12/2014 |

\* cited by examiner

MULTI-DIRECTIONALLY GUIDED ENDOSCOPE

CROSS REFERENCE TO THE RELATED APPLICATIONS

This application is the national of International Application No. PCT/CN2020/141494, filed on Dec. 30, 2020, which is based upon and claims priority to Chinese Patent Application No. 201911405252.1, filed on Dec. 31, 2019, the entire contents of which are incorporated herein by reference.

TECHNICAL FIELD

The present invention belongs to the technical field of endoscopes, and more particularly, relates to a multi-directionally guided endoscope.

BACKGROUND

Endoscopes are common medical devices composed of a bendable part, a light source and a set of lenses. Endoscopes enter the human body through a natural lumen or a small surgical incision of the human body. When in use, endoscopes are introduced into a pre-examined organ to directly observe the changes of the relevant part. Image quality directly affects the use effect of endoscopes, and also marks the development level of the endoscopy. The earliest endoscope was used for rectal examination, where the doctor inserted a hard tube into the patient's anus and observed rectal lesions with the assistance of the light of a candle. Such examination was unable to acquire abundant diagnostic data, painful for the patient, and easy to cause puncture due to the hard instrument. In order to overcome the shortcomings, with the continuous development of endoscopy, different types of endoscopes have been designed for different purposes.

The Chinese patent CN201220463829.1 discloses a multi-directionally bendable endoscope control mechanism and an endoscope. The multi-directionally bendable endoscope control mechanism includes a hose, a main housing, a base, a bending control device and a tightness adjusting device. The tightness adjusting device is provided between the hose and the main housing. The bending control device is connected to a movable control piece on the hose through pulling wires. A motor on the bending control device is fixed to the base through an elastic pressure piece covering the upper surface of the motor. The base is provided with a wire splitter, and the wire splitter is located between a winding wheel and the tightness adjusting device. The wire splitter is provided with a wire guide groove. The upper end face of the wire splitter is provided with a pressure plate. The pulling wires pass through the wire splitter and into the tightness adjusting device. In this patent, the motor is not displaced due to a force in a working state. In addition, because the wire splitter is provided with a wire guide groove and a pressure plate is provided above the wire guide groove, the pulling wires are prevented from coming off, thereby ensuring a normal working state.

However, the pulling operation of the above pulling wires relies on the use of the specific wire splitter, bending control device and tightness adjusting device, which makes the operation complicated. When the pulling wires are connected to an end of a catheter of the endoscope, the end of the catheter can be bent in multiple directions. In the prior art, due to the complicated pulling operation of the pulling wires, the smooth movement of the pulling ends of the pulling wires cannot be guaranteed.

SUMMARY

In order to overcome the shortcomings existing in the prior art, an objective of the present invention is to provide a multi-directionally guided endoscope, which is provided with pulling mechanisms that are simple in structure, convenient to operate, and accurate and stable to pull.

A technical solution adopted by the present invention is as follows:

A multi-directionally guided endoscope includes an endoscope body, where the endoscope body is connected to a catheter; at least four pulling wires are evenly distributed in the endoscope body; one ends of the pulling wires are connected to an end of the catheter away from the endoscope body; the pulling wires are respectively fixed to pulling mechanisms; the pulling mechanisms are respectively sleeved on guide rods; the guide rods are fixed in the endoscope body; the endoscope body is provided with a plurality of elongated grooves; and one ends of the pulling mechanisms respectively extend from the elongated grooves.

Preferably, springs may be respectively connected between the pulling mechanisms and the endoscope body.

Preferably, a pulling sleeve may be sleeved on the endoscope body, and a toggle plate for toggling the pulling mechanisms may be provided in the pulling sleeve.

Preferably, a positioning step may be provided in the pulling sleeve; the positioning step may be provided with a plurality of positioning grooves; and the one ends of the pulling mechanisms extended out of the endoscope body may be respectively engaged in the positioning grooves.

Preferably, the pulling mechanisms respectively include sliders; the sliders may be respectively sleeved on the guide rods; the other ends of the pulling wires may be respectively fixed to the sliders; a toggle block and an engaging block may be fixed to each of the sliders; the toggle block and the engaging block may be located between the toggle plate and the positioning step; and the engaging block may be engaged in each of the positioning grooves.

Preferably, the engaging block includes an elastic rod; one end of the elastic rod may be fixed to each of the sliders, and the other end of the elastic rod may be fixed to an engaging head; and the engaging head may be engaged in each of the positioning grooves.

Preferably, a width of the toggle plate may be greater than a distance between two adjacent pulling mechanisms.

Preferably, a width of the toggle plate may be greater than a distance between two adjacent pulling mechanisms; and there may be eight positioning grooves and four pulling mechanisms.

Preferably, covers may be respectively connected to upper and lower ends of the pulling sleeve.

Preferably, the pulling sleeve may be provided with a handle step for conveniently pulling.

The present invention has the following beneficial effects:

1. In the present invention, at least four pulling wires are evenly distributed in the endoscope body, and the pulling wires are respectively fixed to the pulling mechanisms. When the pulling mechanisms are operated respectively, the pulling wires respectively pull the end of the catheter to bend the catheter in multiple directions, such that the catheter can be advanced in multiple directions. The pulling mechanisms are respectively sleeved on the guide rods. Thus, when the pulling mechanisms are moved, the pulling mechanisms always slide on the guide rods, ensuring that the pulling mechanisms move linearly and smoothly. Accordingly, the pulling wires can move smoothly, and the movement amount of the pulling wires can be accurately controlled. By accurately controlling the moving distance of the pulling wires, the bending degree of the end of the catheter can be controlled, so as to ensure that the advancing direction of the catheter is accurate. In the present invention, the pulling mechanisms are moved manually or through a mechanism, which is convenient to operate, simple in structure and easy to implement.

2. In a natural state, the springs drive the pulling mechanisms to approach the catheter, such that the pulling mechanisms respectively abut against ends of the elongated grooves close to the catheter. In this state, the pulling wires are not pulled, and the end of the catheter is not bent. When the springs push the pulling mechanisms to an exact position, the pulling wires are located at a set position, so as to avoid the displacement of the pulling wires due to accidental touch. Therefore, when the pulling mechanisms are not operated, the pulling wires are located at a set position, and the end of the catheter will not be bent, ensuring that the bending degree of the end of the catheter is controllable.

3. When the pulling sleeve is turned to a certain position, the toggle plate is located above one or more pulling mechanisms. When the pulling sleeve is pulled, the toggle plate in the pulling sleeve pulls a corresponding pulling mechanism to move, thereby pulling a corresponding pulling wire. When the pulling wire is pulled, the end of the catheter is bent toward the direction where the pulled pulling wire is located, so as to control the bending direction of the catheter. With the pulling sleeve, the pulling mechanisms and the pulling wires can be pulled only by turning the pulling sleeve and then pulling the pulling sleeve, which further simplifies the operation and achieves a labor-saving effect.

4. The positioning step is provided with a plurality of positioning grooves, and the pulling mechanisms are engaged in the positioning grooves. When the pulling sleeve is turned, the ends of the pulling mechanisms extended out of the elongated grooves bounce up and snap into the positioning grooves. At this time, the relative positions of the pulling mechanisms and the toggle plate are clear, which is convenient for the toggle plate to accurately pull the pulling mechanisms. This design avoids the problem that when the pulling mechanisms rotate to an edge position of the toggle plate in the absence of the positioning grooves, the pulling mechanisms cannot be pulled accurately. By turning the pulling sleeve, the pulling mechanism currently aligned with the toggle plate can be accurately determined. In this way, the corresponding pulling wire can be pulled accurately, and the bending direction of the end of the catheter can be accurately determined and controlled.

5. The slider is stably movable in a straight line on the guide rod, and the engaging block is engaged in each of the positioning grooves, such that the pulling sleeve can realize accurate positioning. The toggle block and the engaging block are located between the toggle plate and the positioning step. The toggle plate can limit the toggle block, and the pulling mechanism is completely limited. The engaging block can be accurately engaged in the positioning grooves under a pushing force of the toggle plate. When the pulling sleeve is turned, each toggle block is always limited by the toggle plate. The engaging block can first jump out of an initial positioning groove and then be engaged in another positioning groove, thereby realizing accurate displacement of the pulling sleeve. Therefore, the present invention can conveniently determine the direction, so as to accurately control the bending direction of the end of the catheter.

6. The elastic rod can withstand certain bending and rebound. When the pulling sleeve is turned, the engaging head is squeezed, and the elastic rod is bent to a certain extent, such that the engaging head can be disengaged from the positioning groove smoothly. When the engaging head moves into another positioning groove, under an elastic force of the elastic rod, the engaging head is engaged in the positioning grooves. When the turning of the pulling sleeve is stopped, a toggle block moves under the toggle plate of the pulling sleeve. When the pulling sleeve is pulled, a corresponding pulling mechanism and a pulling wire are pulled accurately. The pulling mechanisms and the pulling sleeve can be relatively moved to an accurate position, so as to realize accurate control.

7. The width of the toggle plate is greater than the distance between two adjacent pulling mechanisms. The pulling sleeve can pull two adjacent pulling mechanisms at the same time, so as to pull two pulling wires at the same time. Thus, the end of the catheter is bent toward a middle direction between the two pulling wires. The toggle plate can also pull only one pulling mechanism, such that a corresponding pulling wire is pulled to bend the end of the catheter. With this design, the bending directions of the end of the catheter are double the number of the pulling wires, which reduces the number of the pulling wires and the pulling mechanisms, and simplifies the structure.

8. Since there are eight positioning grooves and four pulling mechanisms, the pulling sleeve has eight positioning directions. The width of the toggle plate is greater than the distance between two adjacent pulling mechanisms. Thus, when the pulling sleeve is moved in case two pulling mechanisms are aligned with the toggle plate, the two adjacent pulling mechanisms are pulled at the same time, and the end of the catheter is bent toward a middle direction between the two pulling wires. When the toggle plate of the pulling sleeve is moved in case one pulling mechanism is aligned with the toggle plate, a corresponding pulling wire is pulled to bend the end of the catheter. The end of the catheter is controlled to bend in eight directions only by the four pulling mechanisms and pulling wires, which simplifies the structure and facilitates control.

9. The covers are respectively connected to the upper and lower ends of the pulling sleeve, and the covers seal the two ends of the pulling sleeve so as to prevent impurities from entering the pulling mechanisms and protect the pulling mechanisms from being stuck or damaged by impurities. The pulling sleeve covers the elongated grooves and the pulling mechanisms so as to protect the pulling mechanisms from damage.

10. The handle step is provided for a user to pull the pulling sleeve, which is convenient for operation. When the pulling sleeve is turned to an appropriate angle, the handle step is hooked manually, and then the handle step is pulled, such that the pulling sleeve is moved as a whole. The toggle plate in the pulling sleeve can pull a corresponding pulling mechanism to move, such that the end of the catheter is pulled and bent by a corresponding pulling wire, which is convenient and labor-saving.

The beneficial effects of the present invention are not limited thereto. For ease of understanding, the beneficial effects of the present invention are described in more detail in the detailed description.

The additional advantages, objectives and features of the present invention will be set forth in part in the following description, and will become apparent in part to those of ordinary skill in the art upon reading the following description, or may be learned from practice of the present invention. The objectives and other advantages of the present invention may be realized by the structures illustrated in the specification, claims and drawings.

Those skilled in the art should understand that the objectives and advantages of the present invention are not limited thereto, and the following description will help to clearly understand the above and other objectives of the present invention.

BRIEF DESCRIPTION OF THE DRAWINGS

To describe the technical solutions in the embodiments of the present invention or in the prior art more clearly, the following briefly describes the drawings required for describing the embodiments or the prior art. Apparently, the drawings in the following description show merely some embodiments of the present invention, and a person of ordinary skill in the art may still derive other drawings from these drawings without creative efforts.

Figure 1:
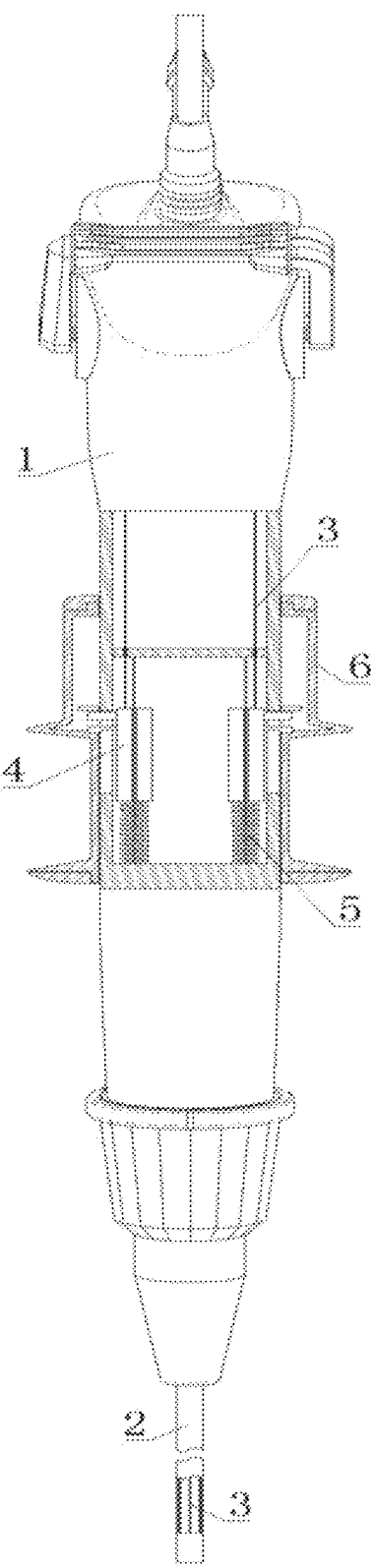
FIG. 1 is a full structural view of a multi-directionally guided endoscope according to the present invention.

Reference Numerals: 1. endoscope body; 2. catheter; 3. pulling wire; 4. pulling mechanism; 5. spring; 6. pulling sleeve; 7. guide rod; 11. elongated groove; 41. slider; 42. toggle block; 43. engaging block; 61. toggle plate; 62. positioning step; 63. positioning groove; 64. cover; 65. handle step; 431. elastic rod; and 432. engaging head.

DETAILED DESCRIPTION OF THE EMBODIMENTS

The embodiments of the present invention are described below in detail. The embodiments are shown in the drawings. The same or similar numerals represent the same or similar elements or elements having the same or similar functions throughout the specification. The embodiments described below with reference to the drawings are illustrative, which are merely intended to explain the present invention, rather than to limit the present invention.

It should be understood that in the description of the present invention, terms such as "first" and "second" are used merely for a descriptive purpose, and should not be construed as indicating or implying relative importance, or implicitly indicating the number of indicated technical features. Thus, features defined with "first" and "second" may explicitly or implicitly include one or more of the features. In the description of the present invention, "multiple" means two or more, unless otherwise specifically defined.

In the present invention, unless otherwise clearly specified, the terms "provided", "connected with", "connected to", and "fixed" should be understood in a broad sense. For example, the connection may be a fixed connection, a detachable connection or an integrated connection, may be a mechanical connection or an electrical connection, may be a direct connection or an indirect connection with use of an intermediate medium, or may be intercommunication between two components. Those of ordinary skill in the art may understand specific meanings of the above terms in the present invention based on a specific situation.

Embodiment 1

Figure 2:
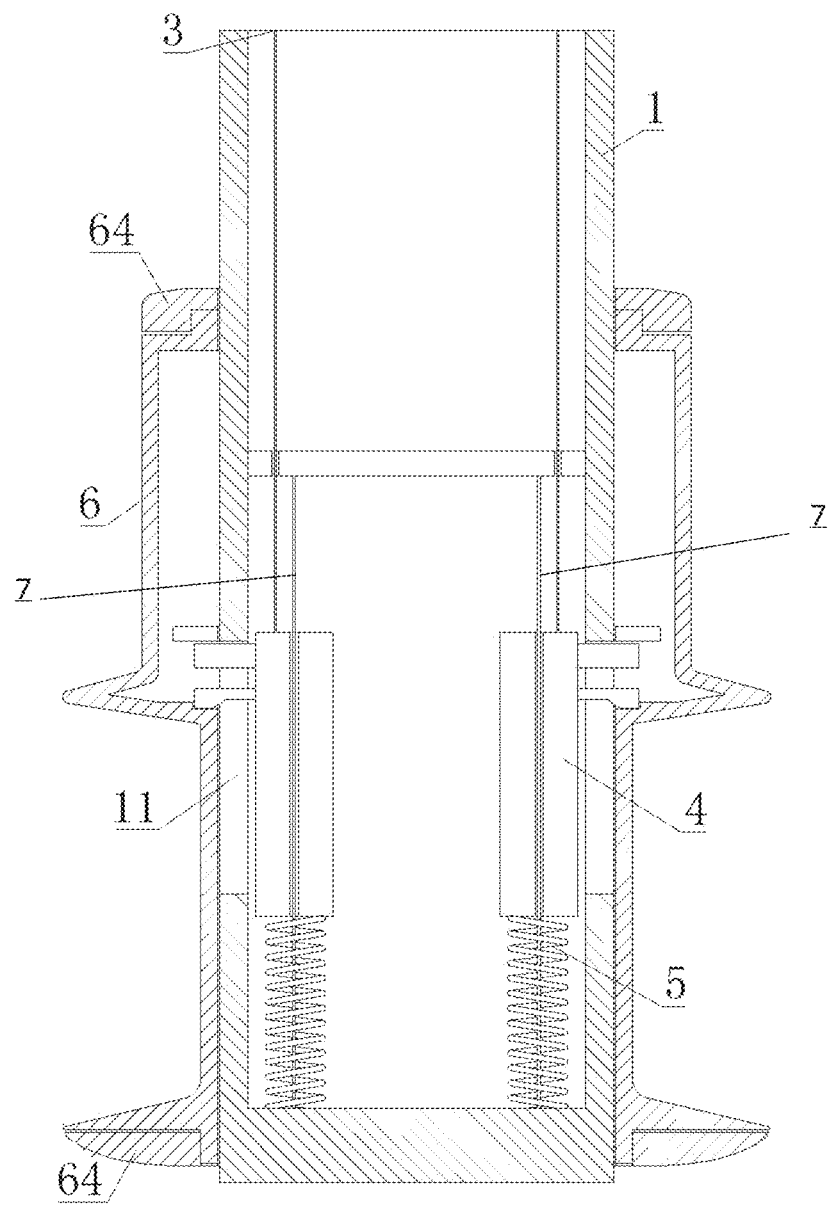
FIG. 2 is a partial structural view of the multi-directionally guided endoscope according to the present invention.

As shown in FIGS. 1 and 2, a multi-directionally guided endoscope includes an endoscope body 1. The endoscope body 1 is connected to a catheter 2. At least four pulling wires 3 are evenly distributed in the endoscope body 1. One ends of the pulling wires 3 are connected to an end of the catheter 2 away from the endoscope body 1. The pulling wires 3 are respectively fixed to pulling mechanisms 4. The pulling mechanisms 4 are respectively sleeved on guide rods 7. The guide rods 7 are fixed in the endoscope body 1. The endoscope body 1 is provided with a plurality of elongated grooves 11. One ends of the pulling mechanisms 4 respectively extend from the elongated grooves 11.

In the present invention, at least four pulling wires 3 are evenly distributed in the endoscope body 1, and the pulling wires 3 are respectively fixed to the pulling mechanisms 4. When the pulling mechanisms 4 are operated respectively, the pulling wires 3 respectively pull the end of the catheter 2 to bend the catheter 2 in multiple directions, such that the catheter 2 can be advanced in multiple directions. The pulling mechanisms 4 are respectively sleeved on the guide rods 7. Thus, when the pulling mechanisms 4 are moved, the pulling mechanisms 4 always slide on the guide rods 7, ensuring that the pulling mechanisms 4 move linearly and smoothly. Accordingly, the pulling wires 3 can move smoothly, and the movement amount of the pulling wires 3 can be accurately controlled. By accurately controlling the moving distance of the pulling wires 3, the bending degree of the end of the catheter 2 can be controlled, so as to ensure that the advancing direction of the catheter 2 is accurate. In the present invention, the pulling mechanisms 4 are moved manually or through a mechanism, which is convenient to operate, simple in structure and easy to implement.

Further, springs 5 are respectively connected between the pulling mechanisms 4 and the endoscope body 1. In a natural state, the springs 5 drive the pulling mechanisms 4 to approach the catheter 2, such that the pulling mechanisms 4 respectively abut against ends of the elongated grooves 11 close to the catheter 2. In this state, the pulling wires 3 are not pulled, and the end of the catheter 2 is not bent. When the springs 5 push the pulling mechanisms 4 to an exact position, the pulling wires 3 are located at a set position, so as to avoid the displacement of the pulling wires 3 due to accidental touch. Therefore, when the pulling mechanisms 4 are not operated, the pulling wires 3 are located at a set position, and the end of the catheter 2 will not be bent, ensuring that the bending degree of the end of the catheter 2 is controllable.

Embodiment 2

Figure 7:
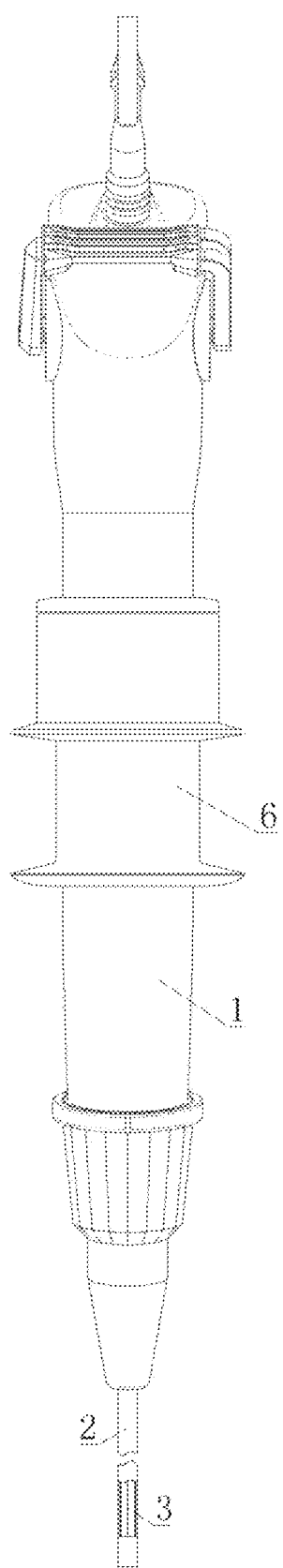
FIG. 7 is a front view of the multi-directionally guided endoscope according to the present invention.

As shown in FIGS. 1, 2 and 7, a multi-directionally guided endoscope includes an endoscope body 1. The endoscope body 1 is connected to a catheter 2. At least four pulling wires 3 are evenly distributed in the endoscope body 1. One ends of the pulling wires 3 are connected to an end of the catheter 2 away from the endoscope body 1. The pulling wires 3 are respectively fixed to pulling mechanisms 4. The pulling mechanisms 4 are respectively sleeved on guide rods 7. The guide rods 7 are fixed in the endoscope body 1. The endoscope body 1 is provided with a plurality of elongated grooves 11. One ends of the pulling mechanisms 4 respectively extend from the elongated grooves 11.

In the present invention, at least four pulling wires 3 are evenly distributed in the endoscope body 1, and the pulling wires 3 are respectively fixed to the pulling mechanisms 4. When the pulling mechanisms 4 are operated respectively, the pulling wires 3 respectively pull the end of the catheter 2 to bend the catheter 2 in multiple directions, such that the catheter 2 can be advanced in multiple directions. The pulling mechanisms 4 are respectively sleeved on the guide rods 7. Thus, when the pulling mechanisms 4 are moved, the pulling mechanisms 4 always slide on the guide rods 7, ensuring that the pulling mechanisms 4 move linearly and smoothly. Accordingly, the pulling wires 3 can move smoothly, and the movement amount of the pulling wires 3 can be accurately controlled. By accurately controlling the moving distance of the pulling wires 3, the bending degree of the end of the catheter 2 can be controlled, so as to ensure that the advancing direction of the catheter 2 is accurate. In the present invention, the pulling mechanisms 4 are moved manually or through a mechanism, which is convenient to operate, simple in structure and easy to implement.

Further, springs 5 are respectively connected between the pulling mechanisms 4 and the endoscope body 1. In a natural state, the springs 5 drive the pulling mechanisms 4 to approach the catheter 2, such that the pulling mechanisms 4 respectively abut against ends of the elongated grooves 11 close to the catheter 2. In this state, the pulling wires 3 are not pulled, and the end of the catheter 2 is not bent. When the springs 5 push the pulling mechanisms 4 to an exact position, the pulling wires 3 are located at a set position, so as to avoid the displacement of the pulling wires 3 due to accidental touch. Therefore, when the pulling mechanisms 4 are not operated, the pulling wires 3 are located at a set position, and the end of the catheter 2 will not be bent, ensuring that the bending degree of the end of the catheter 2 is controllable.

Figure 3:
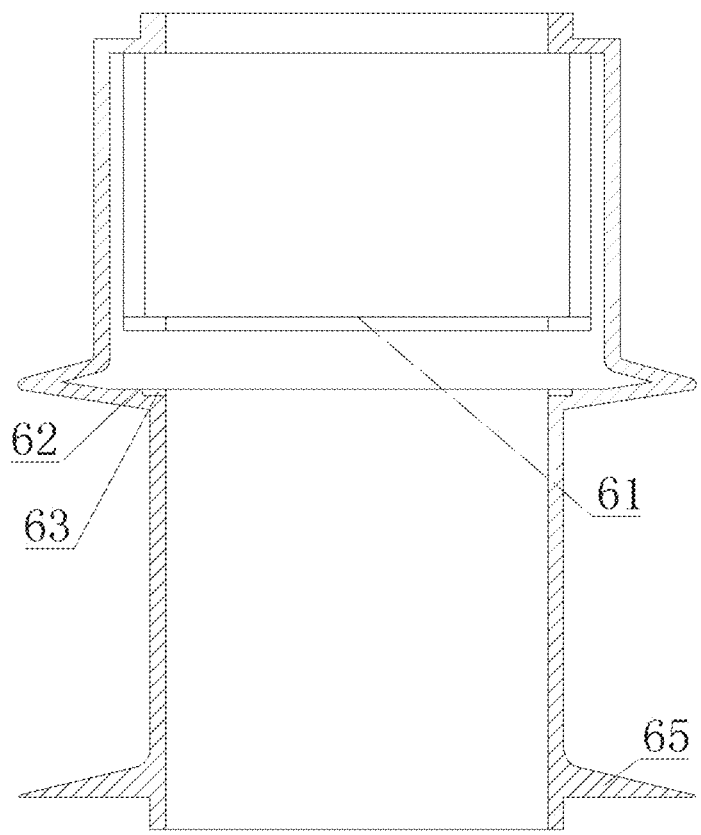
FIG. 3 is a structural view of a pulling sleeve according to the present invention.

Further, as shown in FIG. 3, a pulling sleeve 6 is sleeved on the endoscope body 1, and a toggle plate 61 for toggling the pulling mechanisms 4 is provided in the pulling sleeve 6. When the pulling sleeve 6 is turned to a certain position, the toggle plate 61 is located above one or more pulling mechanisms 4. When the pulling sleeve 6 is pulled, the toggle plate 61 in the pulling sleeve 6 pulls a corresponding pulling mechanism 4 to move, thereby pulling a corresponding pulling wire 3. When the pulling wire 3 is pulled, the end of the catheter 2 is bent toward the direction where the pulled pulling wire 3 is located, so as to control the bending direction of the catheter 2. With the pulling sleeve 6, the pulling mechanisms 4 and the pulling wires 3 can be pulled only by turning the pulling sleeve 6 and then pulling the pulling sleeve 6, which further simplifies the operation and achieves a labor-saving effect.

Figure 6:
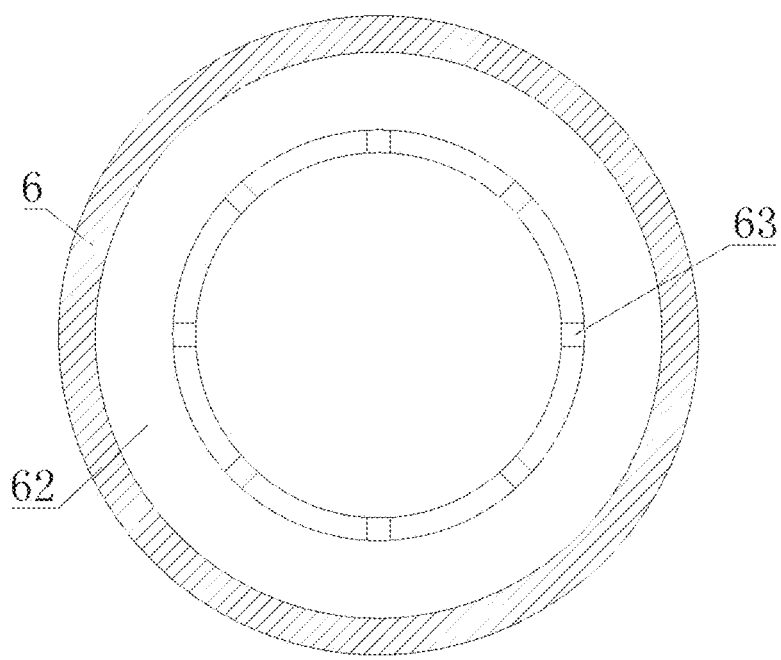
FIG. 6 is a cross-sectional view of the pulling sleeve according to the present invention.

Further, as shown in FIG. 6, a positioning step 62 is provided in the pulling sleeve 6. The positioning step 62 is provided with a plurality of positioning grooves 63. The one ends of the pulling mechanisms 4 extended out of the endoscope body 1 are respectively engaged in the positioning grooves 63. The positioning step 62 is provided with a plurality of positioning grooves 63, and the pulling mechanisms 4 are engaged in the positioning grooves 63. When the pulling sleeve 6 is turned, the ends of the pulling mechanisms 4 extended out of the elongated grooves 11 bounce up and snap into the positioning grooves 63. At this time, the relative positions of the pulling mechanisms 4 and the toggle plate 61 are clear, which is convenient for the toggle plate 61 to accurately pull the pulling mechanisms 4. This design avoids the problem that when the pulling mechanisms 4 rotate to an edge position of the toggle plate 61 in the absence of the positioning grooves 63, the pulling mechanisms 4 cannot be pulled accurately. By turning the pulling sleeve, the pulling mechanism 4 currently aligned with the toggle plate 61 can be accurately determined. In this way, the corresponding pulling wire 3 can be pulled accurately, and the bending direction of the end of the catheter 2 can be accurately determined and controlled.

Figure 4:
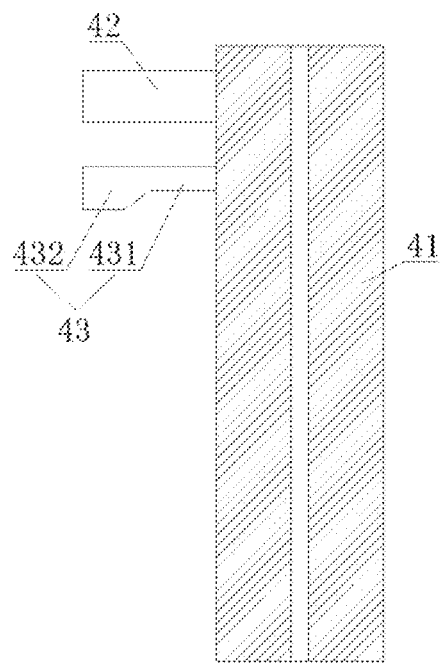
FIG. 4 is a structural view of a pulling mechanism according to the present invention.
Figure 5:
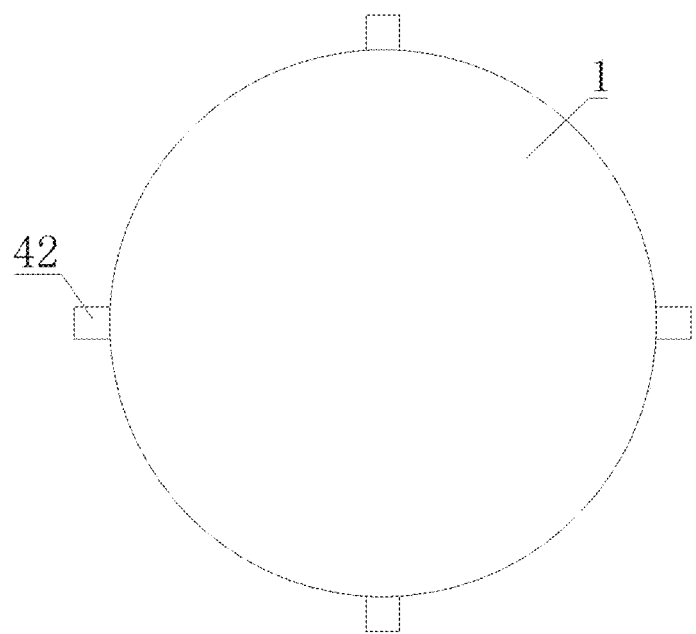
FIG. 5 is a partial top view of the multi-directionally guided endoscope according to the present invention.

Further, as shown in FIGS. 4 and 5, the pulling mechanisms 4 respectively include sliders 41. The sliders 41 are respectively sleeved on the guide rods 7. The other ends of the pulling wires 3 are respectively fixed to the sliders 41. A toggle block 42 and an engaging block 43 are fixed to each of the sliders 41. The toggle block 42 and the engaging block 43 are located between the toggle plate 61 and the positioning step 62. The engaging block 43 is engaged in each of the positioning grooves 63.

The slider 41 is stably movable in a straight line on the guide rod 7, and the engaging block 43 is engaged in each of the positioning grooves 63, such that the pulling sleeve 6 can realize accurate positioning. The toggle block 42 and the engaging block 43 are located between the toggle plate 61 and the positioning step 62. The toggle plate 61 can limit the toggle block 42, and the pulling mechanism 4 is completely limited. The engaging block 43 can be accurately engaged in the positioning groove 63 under a pushing force of the toggle plate 61. When the pulling sleeve 6 is turned, each toggle block 42 is always limited by the toggle plate 61. The engaging block 43 can first jump out of an initial positioning groove 63 and then be engaged in another positioning groove 63, thereby realizing accurate displacement of the pulling sleeve 6. Therefore, the present invention can conveniently determine the direction, so as to accurately control the bending direction of the end of the catheter 2.

Further, the engaging block 43 includes an elastic rod 431. One end of the elastic rod 431 is fixed to each of the sliders 41, and the other end of the elastic rod 431 is fixed to an engaging head 432. The engaging head 432 is engaged in each of the positioning grooves 63.

The elastic rod 431 can withstand certain bending and rebound. When the pulling sleeve 6 is turned, the engaging head 432 is squeezed, and the elastic rod 431 is bent to a certain extent, such that the engaging head 432 can be disengaged from the positioning groove 63 smoothly. When the engaging head 432 moves into another positioning groove 63, under an elastic force of the elastic rod 431, the engaging head 432 is engaged in the positioning groove 63. When the turning of the pulling sleeve 6 is stopped, a toggle block 42 moves under the toggle plate 61 of the pulling sleeve 6. When the pulling sleeve 6 is pulled, a corresponding pulling mechanism 4 and a pulling wire 3 are pulled accurately. The pulling mechanisms 4 and the pulling sleeve 6 can be relatively moved to an accurate position, so as to realize accurate control.

Further, covers 64 are respectively connected to upper and lower ends of the pulling sleeve 6. The covers 64 are respectively connected to the upper and lower ends of the pulling sleeve 6, and the covers 64 seal the two ends of the pulling sleeve 6 so as to prevent impurities from entering the pulling mechanisms 4 and protect the pulling mechanisms 4 from being stuck or damaged by impurities. The pulling sleeve 6 covers the elongated grooves 11 and the pulling mechanisms 4 so as to protect the pulling mechanisms 4 from damage.

Further, the pulling sleeve 6 is provided with a handle step 65 which is convenient for pulling. The handle step 65 is provided for a user to pull the pulling sleeve 6, which is convenient for operation. When the pulling sleeve 6 is turned manually to an appropriate angle, the handle step 65 is hooked manually, and then the handle step 65 is pulled, such that the pulling sleeve 6 is moved as a whole. The toggle plate 61 in the pulling sleeve 6 can pull a corresponding pulling mechanism 4 to move, such that the end of the catheter 2 is pulled and bent by a corresponding pulling wire 3, which is convenient and labor-saving.

Embodiment 3

As shown in FIGS. 1, 2 and 7, a multi-directionally guided endoscope includes an endoscope body 1. The endoscope body 1 is connected to a catheter 2. At least four pulling wires 3 are evenly distributed in the endoscope body 1. One ends of the pulling wires 3 are connected to an end of the catheter 2 away from the endoscope body 1. The pulling wires 3 are respectively fixed to pulling mechanisms 4. The pulling mechanisms 4 are respectively sleeved on guide rods 7. The guide rods 7 are fixed in the endoscope body 1. The endoscope body 1 is provided with a plurality of elongated grooves 11. One ends of the pulling mechanisms 4 respectively extend from the elongated grooves 11.

In the present invention, at least four pulling wires 3 are evenly distributed in the endoscope body 1, and the pulling wires 3 are respectively fixed to the pulling mechanisms 4. When the pulling mechanisms 4 are operated respectively, the pulling wires 3 respectively pull the end of the catheter 2 to bend the catheter 2 in multiple directions, such that the catheter 2 can be advanced in multiple directions. The pulling mechanisms 4 are respectively sleeved on the guide rods 7. Thus, when the pulling mechanisms 4 are moved, the pulling mechanisms 4 always slide on the guide rods 7, ensuring that the pulling mechanisms 4 move linearly and smoothly. Accordingly, the pulling wires 3 can move smoothly, and the movement amount of the pulling wires 3 can be accurately controlled. By accurately controlling the moving distance of the pulling wires 3, the bending degree of the end of the catheter 2 can be controlled, so as to ensure that the advancing direction of the catheter 2 is accurate. In the present invention, the pulling mechanisms 4 are moved manually or through a mechanism, which is convenient to operate, simple in structure and easy to implement.

Further, springs 5 are respectively connected between the pulling mechanisms 4 and the endoscope body 1. In a natural state, the springs 5 drive the pulling mechanisms 4 to approach the catheter 2, such that the pulling mechanisms 4 respectively abut against ends of the elongated grooves 11 close to the catheter 2. In this state, the pulling wires 3 are not pulled, and the end of the catheter 2 is not bent. When the springs 5 push the pulling mechanisms 4 to an exact position, the pulling wires 3 are located at a set position, so as to avoid the displacement of the pulling wires 3 due to accidental touch. Therefore, when the pulling mechanisms 4 are not operated, the pulling wires 3 are located at a set position, and the end of the catheter 2 will not be bent, ensuring that the bending degree of the end of the catheter 2 is controllable.

Further, as shown in FIG. 3, a pulling sleeve 6 is sleeved on the endoscope body 1, and a toggle plate 61 for toggling the pulling mechanisms 4 is provided in the pulling sleeve 6. When the pulling sleeve 6 is turned to a certain position, the toggle plate 61 is located above one or more pulling mechanisms 4. When the pulling sleeve 6 is pulled, the toggle plate 61 in the pulling sleeve 6 pulls a corresponding pulling mechanism 4 to move, thereby pulling a corresponding pulling wire 3. When the pulling wire 3 is pulled, the end of the catheter 2 is bent toward the direction where the pulled pulling wire 3 is located, so as to control the bending direction of the catheter 2. With the pulling sleeve 6, the pulling mechanisms 4 and the pulling wires 3 can be pulled only by turning the pulling sleeve 6 and then pulling the pulling sleeve 6, which further simplifies the operation and achieves a labor-saving effect.

Further, as shown in FIG. 6, a positioning step 62 is provided in the pulling sleeve 6. The positioning step 62 is provided with a plurality of positioning grooves 63. The one ends of the pulling mechanisms 4 extended out of the endoscope body 1 are respectively engaged in the positioning grooves 63. The positioning step 62 is provided with a plurality of positioning grooves 63, and the pulling mechanisms 4 are engaged in the positioning grooves 63. When the pulling sleeve 6 is turned, the ends of the pulling mechanisms 4 extended out of the elongated grooves 11 bounce up and snap into the positioning grooves 63. At this time, the relative positions of the pulling mechanisms 4 and the toggle plate 61 are clear, which is convenient for the toggle plate 61 to accurately pull the pulling mechanisms 4. This design avoids the problem that when the pulling mechanisms 4 rotate to an edge position of the toggle plate 61 in the absence of the positioning grooves 63, the pulling mechanisms 4 cannot be pulled accurately. By turning the pulling sleeve, the pulling mechanism 4 currently aligned with the toggle plate 61 can be accurately determined. In this way, the corresponding pulling wire 3 can be pulled accurately, and the bending direction of the end of the catheter 2 can be accurately determined and controlled.

Further, as shown in FIGS. 4 and 5, the pulling mechanisms 4 respectively include sliders 41. The sliders 41 are respectively sleeved on the guide rods 7. The other ends of the pulling wires 3 are respectively fixed to the sliders 41. A toggle block 42 and an engaging block 43 are fixed to each of the sliders 41. The toggle block 42 and the engaging block 43 are located between the toggle plate 61 and the positioning step 62. The engaging block 43 is engaged in each of the positioning grooves 63.

The slider 41 is stably movable in a straight line on the guide rod 7, and the engaging block 43 is engaged in each of the positioning grooves 63, such that the pulling sleeve 6 can realize accurate positioning. The toggle block 42 and the engaging block 43 are located between the toggle plate 61 and the positioning step 62. The toggle plate 61 can limit the toggle block 42, and the pulling mechanism 4 is completely limited. The engaging block 43 can be accurately engaged in the positioning groove 63 under a pushing force of the toggle plate 61. When the pulling sleeve 6 is turned, each toggle block 42 is always limited by the toggle plate 61. The engaging block 43 can first jump out of an initial positioning groove 63 and then be engaged in another positioning groove 63, thereby realizing accurate displacement of the pulling sleeve 6. Therefore, the present invention can conveniently determine the direction, so as to accurately control the bending direction of the end of the catheter 2.

Further, the engaging block 43 includes an elastic rod 431. One end of the elastic rod 431 is fixed to each of the sliders 41, and the other end of the elastic rod 431 is fixed to an engaging head 432. The engaging head 432 is engaged in each of the positioning grooves 63.

The elastic rod 431 can withstand certain bending and rebound. When the pulling sleeve 6 is turned, the engaging head 432 is squeezed, and the elastic rod 431 is bent to a certain extent, such that the engaging head 432 can be disengaged from the positioning groove 63 smoothly. When the engaging head 432 moves into another positioning groove 63, under an elastic force of the elastic rod 431, the engaging head 432 is engaged in the positioning groove 63. When the turning of the pulling sleeve 6 is stopped, a toggle block 42 moves under the toggle plate 61 of the pulling sleeve 6. When the pulling sleeve 6 is pulled, a corresponding pulling mechanism 4 and a pulling wire 3 are pulled accurately. The pulling mechanisms 4 and the pulling sleeve 6 can be relatively moved to an accurate position, so as to realize accurate control.

Further, a width of the toggle plate 61 is greater than a distance between two adjacent pulling mechanisms 4. There are eight positioning grooves 63 and four pulling mechanisms 4. Since there are eight positioning grooves 63 and four pulling mechanisms 4, the pulling sleeve 6 has eight positioning directions. The width of the toggle plate 61 is greater than the distance between two adjacent pulling mechanisms 4. Thus, when the pulling sleeve 6 is moved in case two pulling mechanisms 4 are aligned with the toggle plate 61, the two adjacent pulling mechanisms 4 are pulled at the same time, and the end of the catheter 2 is bent toward a middle direction between the two pulling wires 3. When the toggle plate 61 of the pulling sleeve 6 is moved in case one pulling mechanism 4 is aligned with the toggle plate 61, a corresponding pulling wire 3 is pulled to bend the end of the catheter 2. The end of the catheter 2 is controlled to bend in eight directions only by the four pulling mechanisms 4 and pulling wires 3, which simplifies the structure and facilitates control.

Further, covers 64 are respectively connected to upper and lower ends of the pulling sleeve 6. The covers 64 are respectively connected to the upper and lower ends of the pulling sleeve 6, and the covers 64 seal the two ends of the pulling sleeve 6 so as to prevent impurities from entering the pulling mechanisms 4 and protect the pulling mechanisms 4 from being stuck or damaged by impurities. The pulling sleeve 6 covers the elongated grooves 11 and the pulling mechanisms 4 so as to protect the pulling mechanisms 4 from damage.

Further, the pulling sleeve 6 is provided with a handle step 65 which is convenient for pulling. The handle step 65 is provided for a user to pull the pulling sleeve 6, which is convenient for operation. When the pulling sleeve 6 is turned to an appropriate angle, the handle step 65 is hooked manually, and then the handle step 65 is pulled, such that the pulling sleeve 6 is moved as a whole. The toggle plate 61 in the pulling sleeve 6 can pull a corresponding pulling mechanism 4 to move, such that the end of the catheter 2 is pulled and bent by a corresponding pulling wire 3, which is convenient and labor-saving.

The present invention is not limited to the above optional embodiments, and those skilled in the art may derive other products in various forms under the enlightenment of the present invention. However, regardless of any changes in the shape or structure, any technical solutions falling within the scope of the claims of the present invention should fall within the protection scope of the present invention.

What is claimed is:

1. A multi-directionally guided endoscope, comprising an endoscope body, wherein
   the endoscope body is connected to a catheter;
   at least four pulling wires are evenly distributed in the endoscope body, wherein the at least four pulling wires each contain first ends and second ends, wherein the first ends are directionally away from the proximal end of the endoscope body;
   the first ends of the at least four pulling wires are connected to an end of the catheter, wherein the end of the catheter is away from the endoscope body;
   the at least four pulling wires are respectively fixed to a plurality pulling mechanisms;
   the plurality of pulling mechanisms are respectively sleeved on a plurality of guide rods;
   the plurality of guide rods are fixed in the endoscope body;
   the endoscope body is provided with a plurality of elongated grooves;
   first ends of the pulling mechanisms respectively extend from the plurality of elongated grooves;
   a pulling sleeve is sleeved on the endoscope body, and a toggle plate for pulling the pulling mechanisms, thereby causing the pulling mechanisms to pull a corresponding pulling wire, is provided in the pulling sleeve;
   a positioning step is provided in the pulling sleeve;
   the positioning step is provided with a plurality of positioning grooves;
   the first ends of the pulling mechanisms are respectively engaged in the plurality of positioning grooves, wherein the first ends of the pulling mechanisms are directionally away from the proximal end of the endoscope body;
   the pulling mechanisms respectively comprise sliders;
   the sliders are respectively sleeved on the guide rods;
   the second ends of the at least four pulling wires are respectively fixed to the sliders;
   a toggle block and an engaging block are fixed to each of the sliders;
   the toggle block and the engaging block are located between the toggle plate and the positioning step; and
   the engaging block is engaged in each of the positioning grooves.

2. The multi-directionally guided endoscope according to claim 1, wherein
   springs are respectively connected between the pulling mechanisms and the endoscope body.

3. The multi-directionally guided endoscope according to claim 2, wherein
   the pulling sleeve is provided with a handle step for conveniently pulling.

4. The multi-directionally guided endoscope according to claim 1, wherein
   the engaging block comprises an elastic rod;
   a first end of the elastic rod is fixed to each of the sliders, and a second end of the elastic rod is fixed to an engaging head; and
   the engaging head is engaged in each of the positioning grooves.

5. The multi-directionally guided endoscope according to claim 4, wherein
   the pulling sleeve is provided with a handle step for conveniently pulling.

6. The multi-directionally guided endoscope according to claim 1, wherein
   a width of the toggle plate is greater than a distance between two adjacent pulling mechanisms.

7. The multi-directionally guided endoscope according to claim 6, wherein
   the pulling sleeve is provided with a handle step for conveniently pulling.

8. The multi-directionally guided endoscope according to claim 1, wherein
a width of the toggle plate is greater than a distance between two adjacent pulling mechanisms; wherein there are eight positioning grooves and four pulling mechanisms.

9. The multi-directionally guided endoscope according to claim 8, wherein
the pulling sleeve is provided with a handle step for conveniently pulling.

10. The multi-directionally guided endoscope according to claim 1, wherein
covers are respectively connected to upper and lower ends of the pulling sleeve.

11. The multi-directionally guided endoscope according to claim 10, wherein the pulling sleeve is provided with a handle step for conveniently pulling.

12. The multi-directionally guided endoscope according to claim 1, wherein
the pulling sleeve is provided with a handle step for conveniently pulling.

\* \* \* \* \*